United States Patent [19]

Layer

[11] 3,940,364

[45] Feb. 24, 1975

[54] NAPHTHOFURANYLNAPHTHOL STABILIZERS

[75] Inventor: Robert W. Layer, Cuyahoga Falls, Ohio

[73] Assignee: The B. F. Goodrich Company, Akron, Ohio

[22] Filed: May 2, 1975

[21] Appl. No.: 573,818

[52] U.S. Cl. .................... 260/45.8 A; 260/346.2 M
[51] Int. Cl.$^2$............................................ C08J 3/20
[58] Field of Search ........ 260/45.8 A, 346.2 M, 800

[56] References Cited
UNITED STATES PATENTS

| | | | |
|---|---|---|---|
| 2,235,629 | 3/1941 | Clifford ....................... | 260/346.2 M |
| 2,682,473 | 6/1954 | Thompson et al. .......... | 260/346.2 M |
| 3,095,426 | 6/1963 | Peck ............................ | 260/45.8 A |
| 3,598,842 | 8/1971 | Martini ....................... | 260/346.2 M |

OTHER PUBLICATIONS

Monatsch, 73, (1940), pp. 45 to 56, Dischendorfer.

*Primary Examiner*—V. P. Hoke
*Attorney, Agent, or Firm*—J. Hughes Powell, Jr.; Alan A. Csontos

[57] ABSTRACT

Naphthofuranylnaphthols are produced by (1) reacting glyoxal with a naphthol in the presence of an acidic catalyst to form an acetal, and (2) thereafter partially hydrolyzing the acetal with an acidic or basic catalyst. Naphthofuranylnaphthols are effective stabilizers of organic materials against the deleterious effects of oxygen, heat, and light. The stability of dienic polymers and styreneacrylonitrile copolymers is particularly enhanced by incorporating stabilizing amounts of naphthofuranylnaphthols.

22 Claims, No Drawings

NAPHTHOFURANYLNAPHTHOL STABILIZERS

BACKGROUND OF THE INVENTION

Dischendorfer, 73 Monatsch. 45 (1940), teaches preparation of 1-[1-naphtho(2,1-b)furanyl]-2-naphthol without discussion of utility. New stabilizers and new stabilized organic compositions are desired.

SUMMARY OF THE INVENTION

Naphthofuranylnaphthols are effective stabilizers of a wide variety of organic materials against the deleterious effects of oxygen, heat and visible or ultraviolet light. The naphthofuranylnaphthols are especially useful as nonstaining stabilizers for dienic polymers and styreneacrylonitrile copolymers. Naphthofuranylnaphthols suitable for use in this invention have the formula

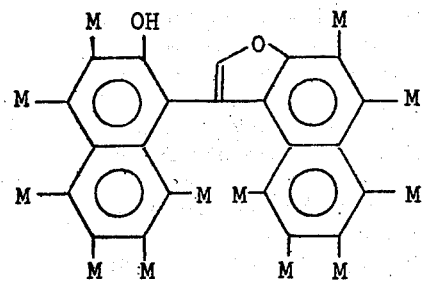

wherein each M may be hydrogen, halogen or an alkyl group containing from one to eight carbon atoms.

DETAILED DESCRIPTION

Naphthofuranylnaphthols suitable for use as stabilizers have the formula below and are numbered as shown:

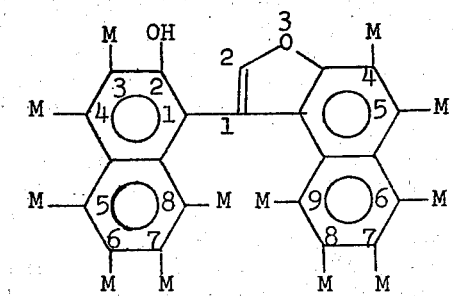

wherein each M may be hydrogen, halogen or an alkyl group containing from one to eight carbon atoms. More preferably, at least six M's are hydrogen and each of the remaining M's is bromo, chloro or an alkyl group containing from one to eight carbon atoms. Even more preferably at least six M's are hydrogen and each of the remaining M's is an alkyl group containing from one to four carbon atoms. Most preferred are naphthofuranylnaphthols wherein at least eight M's are hydrogen but at least two of the remaining M's are alkyl groups containing from one to four carbon atoms. Examples of suitable naphthofuranylnaphthols include 1-[1-naphtho(2,1-b)furanyl]-2-naphthol, 1-[7-t-butyl-1-naphtho(2,1-b)furanyl]-6-t-butyl-2-naphthol, 1-[4,7-di-t-butyl-1-naphtho(2,1-b)furanyl]-3,6-di-t-butyl-2-naphthol, and 1-[6,7,8,9-tetrahydro-1-naphtho(2,1-b)furanyl]-5,6,7,8-tetrahydro-2-naphthol, and the like. Excellent results were obtained using 1-[1-naphtho(2,1-b)-furanyl]-2-naphthol, 1-[7-t-butyl-1-naphtho(2,1-b)furanyl]-6-t-butyl-2-naphthol, 1-[4,7-di-t-butyl-1-naphtho(2,1-b)furanyl]-3,6-di-t-butyl-2-naphthol, and 1-[6,7,8,9-tetrahydro-1-naphtho(2,1-b)furanyl]-5,6,7,8-tetrahydro-2-naphthol. Suitable naphthofuranylnaphthols may be used in an amount from about 0.1 part to about 10 parts by weight, more preferably from about 0.5 to about 5 parts by weight, per 100 parts by weight of organic material to be stabilized.

Naphthofuranylnaphthols are produced by first reacting glyoxal with a naphthol in the presence of an acidic catalyst at a temperature from about 0°C. to about 100°C., more preferably from about 0°C. to about 50°C. An acetal is formed during the first step of the reaction, with acetal yield decreasing substantially if reaction temperature is above 50°C. during the first step. After acetal formation is completed, the second reaction step is performed. Water may be added to the reaction mixture, and the mixture is refluxed in order to hydrolyze the acetal and form a naphthofuranylnaphthol. Alternatively, a solid acetal may be separated from the reaction mixture by filtration in some cases and the acetal thereafter hydrolyzed by refluxing in the presence of an acid or base catalyst.

Naphthols used in the above process preferably have one unsubstituted position adjacent to a hydroxyl group, but certain groups such as t-butyl and the like may occupy an adjacent position and are displaced during acetal formation if the other adjacent position is occupied by another substituent. Suitable naphthols for use in the above process include 2-naphthol, 6-t-butyl-2-naphthol, 3,6-di-t-butyl-2-naphthol, 5,6,7,8-tetrahydro-2-naphthol, 6-bromo-2-naphthol, and the like. Excellent results were obtained using 2-naphthol, 6-t-butyl-2-naphthol, 3,6-di-t-butyl-2-naphthol, and 5,6,7,8-tetrahydro-2-naphthol.

The glyoxal may be used in the anhydrous form but the commercial aqueous solutions of glyoxal are more preferably used. Derivatives of glyoxal which can generate glyoxal in situ may also be used, such as glyoxal.-NaHSO$_4$. The glyoxal may be used in a molar ratio to the naphthol from about 1/10 to about 10/1. More preferably, the ratio is about 1/2.

Acids which may be used to catalyze the reaction of glyoxal with naphthols to form acetals include organic acids containing one to 12 carbon atoms such as acetic acid, propionic acid, benzoic acid, monoesters and diesters of orthophosphoric acid, alkaryl sulfonic acids such as p-toluenesulfonic acid, and the like; inorganic acids capable of releasing protons such as boric acid, hydrochloric acid, phosphoric acid, sulfuric acid, and the like; acid activated clays capable of releasing protons such as Retrol (produced by Filtrol Corp.), bentonite, and the like; acidic resins capable of releasing protons such as Dowex 50-X10 (a cationic exchange resin which is a sulfonated copolymer of styrene and divinylbenzene and is produced by Dow Chemical Company), and the like; and Lewis acids capable of accepting electrons such as aluminum chloride, zinc chloride, boron trifluoride, and the like. The amount of acid catalyst used may be as little as about 0.01% based on total reactant weight, or the catalyst may be used as the solvent in which the reaction is run. Mixtures of acids may also be used. Excellent results were obtained using mixtures of acetic acid and sulfuric acid, zinc chloride and hydrochloric acid, and p-toluenesulfonic acid and acetic acid.

The acids described above may also be used at higher temperatures to catalyze hydrolysis of the acetals in the second reaction step, thereby forming naphthofuranylnaphthols. Bases may be used in place of acids in the second reaction step. Suitable bases include inorganic bases such as sodium hydroxide, potassium hydroxide, and the like. Excellent results were obtained using potassium hydroxide.

Acetic acid is a preferred solvent for these reactions because of its availability, boiling point, water miscibility, ability to dissolve a wide variety of naphthols, and catalytic effect on the reaction. The reaction may also be run in other solvents which include carboxylic acids such as o-toluic acid, esters such as n-butyl acetate, ethers such as bis[2-(2-methoxyethoxy)ethyl]ether, alcohols such as 1-pentanol, ketones such as benzophenone, and the like. The reaction may also be run in a two-phase system where one reactant is soluble in one phase and the other reactant is soluble in a second phase, such as a hydrocarbon and water system. An emulsifying agent may be used to facilitate the reaction in the two-phase system.

A preferred method for producing naphthofuranylnaphthols comprises mixing glyoxal and a naphthol with a major amount of acetic acid and a minor amount of sulfuric acid. The reaction mixture is stirred and cooled below 30°C. for about 1 to 3 hours. After that time, the temperature is raised to about 50°C., and the reaction is continued for about 0.5 to three more hours in order to complete acetal formation. The second reaction step is performed by adding water to the acetal reaction mixture and heating to reflux temperature. After about 1 to 5 hours, the acetal is acid-hydrolyzed substantially to a naphthofuranylnaphthol.

Another preferred method for performing the second reaction step (hydrolysis) comprises separating a solid acetal from the reaction mixture by filtration, mixing the acetal with water and an acid or base, and acid-hydrolyzing or base-hydrolyzing the acetal to a naphthofuranylnaphthol. Refluxing is generally required for acidic hydrolysis, but basic hydrolysis can be performed by simply warming the mixture to be hydrolyzed at about 50° – 100°C. in a dimethyl sulfoxide solution.

The naphthofuranylnaphthol product may be separated from the hydrolysis mixture by any of several methods. If the product is a solid it can be filtered and optionally washed with a solvent such as hexane or water. If the product is an oil it can be extracted with an aromatic solvent such as benzene. If acidic hydrolysis is used, the extract can be washed with a weak base or a basic salt solution such as $Na_2CO_3$ in water. If basic hydrolysis is used, the extract can be washed with a weak acid or an acidic salt solution in water such as $(NH_4)_2SO_4$ in water. The extract can then be distilled to obtain a substantially pure naphthofuranylnaphthol.

Naphthofuranylnaphthols within the scope of the formula recited heretofore are effective stabilizers of a wide variety of organic materials against the deleterious effects of oxygen, heat and visible or ultraviolet light. The naphthofuranylnaphthols are nonstaining stabilizers of both natural and synthetic polymers, such as uncured and vulcanized dienic polymers. The dienic polymers are sulfurvulcanizable and may contain about 0.5% to about 50% by weight of olefinic ($>C=C<$) unsaturation based upon total polymer weight. The olefinic groups may be in the polymeric main chain (backbone) or in pendant (side-chain) groups, or both. Examples of suitable dienic polymers include polymers such as natural rubber, cis-polyisoprene, cispolybutadiene (CB), acrylonitrile-butadiene-styrene copolymers (ABS), butadiene-acrylonitrile rubbers (NBR), isoprene-acrylonitrile rubbers, polyisobutylene, polychloroprene, butadiene-styrene rubbers (SBR), isoprene-styrene rubbers, and the like. Also suitable are polymers such as isoprene-isobutylene (butyl) rubbers, copolymers of conjugated dienes with lower alkyl and alkoxy acrylates such as ethyl acrylate, butyl acrylate, methoxyethyl acrylate, and the like, and ethylene-propylene-diene polymers (EPDM) containing from about 0.5 percent to about 20 percent by weight of at least one dienic termonomer. Suitable EPDM dienic termonomers include conjugated dienes such as butadiene, 1,3-pentadiene, and the like; non-conjugated dienes such as 1,4-pentadiene, 1,4-hexadiene, and the like; cyclic dienes such as cyclopentadiene, dicyclopentadiene, and the like; and alkenyl norbornenes such as 5-ethylidene-2-norbornene, and the like.

The dienic polymers may be vulcanized by methods known to the art. Suitable vulcanizing agents include elemental sulfur and compounds capable of yielding elemental sulfur such as tetramethylthiuram disulfide, tetraethylthiuram disulfide, dipentamethylenethiuram hexasulfide, and the like.

A broad range of compounding ingredients can be used in the dienic polymer vulcanizates, including sulfur-containing and nitrogen-containing accelerators. Examples of suitable accelerators include metal salts of dialkyl, diaryl and alkaryl dithiocarbamates such as bismuth, copper, lead and zinc dimethyl dithiocarbamates, cadmium, selenium, tellurium and zinc diethyl dithiocarbamates, sodium and zinc dibutyl dithiocarbamates, zinc ethyl phenyl dithiocarbamate, zinc dibenzyl dithiocarbamate, and the like; other dithiocarbamates such as piperidinium pentamethylene dithiocarbamate, N-cyclohexylethyl ammonium cyclohexylethyl dithiocarbamate, N-pentamethylene-ammonium-N-pentamethylene dithiocarbamate, and the like; benzothiazoles such as 2-mercaptobenzothiazole and the zinc salt thereof, 2,2'-benzothiazyl disulfide, 2-morpholinothiobenzothiazole, 2-(2,6-dimethyl-4-morpholinothio)-benzothiazole, and the like; benzothiazole-sulfenamides such as N-diethyl-2-benzothiazyl sulfenamide, N-t-butyl-2-benzothiazole sulfenamide, N-cyclohexyl-2-benzothiazole sulfenamide, N-oxydiethylene-2-benzothiazole sulfenamide, and the like; thiuram sulfides such as tetramethyl thiuram disulfide, tetraethyl thiuram disulfide, dimethyl diphenyl thiuram disulfide, dipentamethylene thiuram hexasulfide, and the like; thioureas such as ethylene thiourea, trimethyl thiourea, N,N'-diethyl thiourea, N,N'-dibutyl thiourea, N,N'-diphenyl thiourea, and the like; morpholines such as 4,4'-dithiomorpholine, and the like; polyamines such as triethylene diamine, hexamethylene tetraamine, tricretonylidene tetraamine, and the like; aldehyde-amine condensation products such as acetaldehyde-ammonia, heptaldehyde-ammonia, butyraldehyde-aniline, and the like; imidazolines such as 2-mercaptoimidazoline, and the like; and guanidines such as diphenyl guanidine, di-o-tolyl guanidine, and the like. Excellent results were obtained using 2-morpholinothiobenzothiazole.

Naphthofuranylnaphthols within the scope of the formula recited heretofore are also effective nonstaining antioxidants in styrene-acrylonitrile copolymers. Suitable copolymers for use in the compositions of this invention contain polymerized therein (1) from about 50% to about 90% by weight based upon total copolymer weight of styrene, or at least one alkyl styrene, alkoxy styrene or halostyrene, or a mixture thereof, wherein the alkyl or alkoxy group contains from one to eight carbon atoms, (2) from about 10% to about 50% by weight based upon total copolymer weight of at least one vinyl nitrile having the formula

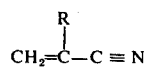

wherein R is hydrogen or an alkyl radical containing from one to three carbon atoms, and (3) from 0% to about 20% by weight based upon total copolymer weight of at least one other monoolefin. Preferred alkyl styrenes are those wherein an alkyl group contains from one to six carbon atoms, more preferably from one to four carbon atoms. Preferred alkoxy styrenes are those wherein an alkoxy group contains from one to six carbon atoms, more preferably from one to four carbon atoms. Preferred halostyrenes are those wherein a halogen group is chloro or bromo. Examples of suitable alkyl styrenes, alkoxy styrenes and halostyrenes include methyl styrene, ethyl styrene, methoxyethylstyrene, chlorostyrene, dichlorostyrene, and the like. Examples of suitable vinyl nitriles include acrylonitrile, methacrylonitrile, ethacrylonitrile, and the like. Excellent results were obtained using copolymers of styrene and acrylonitrile.

Other compounding ingredients usable in the dienic polymer compositions and styrene-acrylonitrile copolymers include fillers such as carbon blacks, calcium and magnesium carbonates, calcium and barium sulfates, aluminum silicates, silicon dioxide, phenol-formaldehyde and polystyrene resins, asbestos and the like; plasticizers and extenders including dialkyl and diaryl acid esters such as diisobutyl, diisooctyl, diisodecyl and dibenzyl oleates, stearates, sebacates, azelates, phthalates, and the like, and naphthenic and paraffinic oils, castor oil, tall oil, and the like; and antioxidants, antiozonants and stabilizers such as di-$\beta$-naphthyl-p-phenylenediamine, phenyl-$\beta$-naphthylamine, N,N'-di-(2-octyl)-p-phenylenediamine, 2,2'-methylene-bis(4-methyl-6-t-butylphenol), 2,6-di-t-butyl-p-cresol, 2,2'-thiobis(4-methyl-6-t-butylphenol), distearyl thiodipropionate, dilauryl thiodipropionate, 2,4-bis(4-hydroxy-3,5-t-butylphenoxy)-6-(n-octylthio)-1,3,5-triazine, tetrakis methylene 3-(3',5'-di-t-butyl-4'-hydroxyphenyl)-propionate methane, 4-isopropylamino diphenylamine, tri(nonylated phenyl)phosphite, and the like. Other compounding ingredients may also be used, such as pigments, tackifiers, flame retardants, fungicides, and the like.

In addition to polymer materials, the present naphthofuranylnaphthols act to stabilize a wide variety of other organic materials. Such materials include: waxes; synthetic and petroleum-derived lubricating oils and greases; animal oils such as fat, tallow, lard, cod-liver oil, sperm oil and the like; vegetable oils such as castor, linseed, peanut, palm, cotton seed, and the like; fuel oil; diesel oil; gasoline; and the like.

The following examples illustrate the present invention more fully.

EXAMPLE 1

Preparation of 1-[1-naphtho(2,1-b)-furanyl]-2-naphthol

2-Naphthol (43 g. or 0.3 mole), 40% aqueous glyoxal (22.5 g. or 0.15 mole), and p-toluenesulfonic acid (30 g. or 0.16 mole) were dissolved in glacial acetic acid (200 ml.). The mixture was stirred for about 3 hours with cooling as necessary to keep reaction temperature at 30°C. The mixture was heated thereafter to 50°C., stirred for about 0.5 hour, cooled, and filtered to separate 40 g. acetal having a melting point of 234°–239°C. The filtrate was recycled twice to the reaction mixture to produce 66 g. more of acetal. One liter of water then was mixed with the remaining filtrate and 28 g. more of acetal was separated by filtration. Total acetal yield was 98%.

A portion of the acetal (30 g. or 0.12 mole) was dissolved in 250 ml. of acetic acid, and 20 ml. concentrated HCl was added to the solution. The solution was heated to about 80°C. for about 1.5 hours and thereafter poured into about 1 liter of water. A solid was filtered from the solution and found to have a melting point of 176°–180°C. Its NMR and IR spectra were consistent with the structural assignment of 1-[1-naphtho(2,1-b)furanyl]-2-naphthol. Calculated: C,85.14; H,4.55. Found: C,85.99; H,4.45.

EXAMPLE 2

Preparation of 1-[7-t-butyl-1-naphtho(2,1-b)-furanyl]-6-t-butyl-2-naphthol.

6-t-butyl-2-naphthol (40 g. or 0.2 mole), 40% aqueous glyoxal (15 g. or 0.1 mole) and 150 ml. of acetic acid was treated with 15 ml. of concentrated sulfuric acid while maintaining the temperature at 30°C. for 2 hours. The mixture was then held at 50°C. for 0.5 hour, cooled, poured into water, filtered, and washed with water to give the crude acetal intermediate. This acetal (10 g.) was refluxed with 75 ml. of acetic acid and 5 ml. of concentrated hydrochloric acid for 2 hours, cooled, poured into 500 ml. of water, filtered and washed with water to give 5 grams of a yellow solid product. Its IR spectrum was consistent with its structural assignment of 1-[7-t-butyl-1-naphtho(2,1-b)furanyl]-6-t-butyl-2-naphthol.

EXAMPLE 3

Preparation of 1-[4,7-di-t-butyl-1-naphtho(2,1-b)furanyl]-3,6-di-t-butyl-2-naphthol 3,6-Di-t-butyl-2-naphthol (22 g. or 0.09 mole), 30% aqueous glyoxal (12 g. or 0.08 mole) and 100 ml. of acetic acid were treated with 10 ml. of concentrated sulfuric acid at 30°C. for 2 hours, then heated for 0.5 hour at 50°C., cooled, poured into 500 ml. of water, filtered and washed with water to give 20 g. of the desired acetal. This acetal (19 g.) was heated at 100°C. for 1 hour with 200 ml. of dimethylsulfoxide, 100 ml. of methanol, and 15 g. (0.27 mole) of potassium hydroxide, allowed to cool to room temperature, poured into 1.5 liters of water, acidified with 23 ml. of concentrated hydrochloric acid, filtered, washed with water, and dried to give 19 g. of product (m.p. 140° – 160°C.). Its IR and NMR spectra were consistent with the assigned structure of 1-[ 4,7-di-t-butyl-1-naptho(2,1-b)furanyl]-3,6-di-t-butyl-2-naphthol.

EXAMPLE 4

Preparation of 1-[6,7,8,9-tetrahydro-1-naptho(2,1-b)furanyl]-5,6,7,8-tetrahydro-2-naphthol 5,6,7,8-Tetrahydro-2-naphthol (45 g. or 0.3 mole), 40% aqueous glyoxal (22.5 g. or 0.15 mole) and 200 ml. of acetic acid were treated with 80 ml. of concentrated sulfuric acid while maintaining the temperature at 30°C. for 2 hours, then at 50°C. for 0.5 hour to give a slurry. A solid was filtered, washed with water, and dried to give 48 g. of crude acetal. This acetal was recrystallized from an ethanolbenzene-acetone mixture to give white needles (m.p. 229°–235°C.). The NMR spectrum was consistent with an acetal structure. This acetal (43 g.) was refluxed for 2 hours with 180 ml. of acetic acid, 4 ml. of water, and 1 ml. of concentrated sulfuric acid. The mixture was cooled, poured into 1 liter of water, and the crude product separated to give 37 g. of viscous black oil. The IR spectrum of the oil was consistent with the assigned structure of 1-[6,7,8,9-tetrahydro-1-naphtho(2,1-b)furanyl]-5,6,7,8-tetrahydro-2-naphthol.

EXAMPLES 5 – 19

Examples 5–19 demonstrate stabilizing properties of naphthofuranylnaphthols in cured rubber vulcanizates. A masterbatch was prepared by mixing the following materials in a Banbury mixer:

TABLE I

| Materials | Parts by Weight |
|---|---|
| Ribbed Smoked Sheet | 100.0 |

TABLE I-continued

| Materials | Parts by Weight |
|---|---|
| Natural Rubber HAF Carbon Black | 50.0 |
| Zinc Oxide | 5.0 |
| Stearic Acid | 3.0 |
| Sulfur | 2.5 |
| | 160.5 |

In each example, 176 g. of the masterbatch described in Table I was compounded and cured with 1.1 gram of 2-morpholinothiobenzothiazole accelerator and 1.1 gram of a given stabilizer. The compounding and curing procedure was as follows. A 4-inch, 2-roll mill was heated to 160°F. and each ingredient was charged to the mill in the order listed with thorough milling between each addition. Each milled rubber composition was sheeted off the mill and cut into approximate 6 in. × 6 in. × 0.090 in. sections. The sections were wrapped separately in aluminum foil and cured for 35 minutes at 302°F.

Physical testing of the vulcanizates was performed and the results are set forth in Tables II, III and IV. 300% Modulus, tensile strength, and ultimate elongation were determined according to ASTM D412-68 using Die C dumbbells. Test tube aging was performed according to ASTM D865-62 for 24 hours at 100°C. Crack Growth Test results in Table II were measured using the B. F. Goodrich Rotating Ring Crack Growth Test described in 38 Rubber Chemistry & Technology 719 (1965). Standard conditions used for the latter test were 70°C., 3 lbs. load and 300 cycles/minute.

The data in Tables II, III and IV indicates that the naphthofuranylnaphthols tested have stabilizing properties as good as or better than control stabilizers when tested in cured rubber vulcanizates.

TABLE II

Aging Characteristics of Naphthofuranylnaphthols in Natural Rubber Vulcanizates

| Example | Compound | Starting Naphthol | Test Tube Aging (24 hrs. at 100°C.) | | | | | | Crack Growth Test | |
|---|---|---|---|---|---|---|---|---|---|---|
| | | | 200% Modulus | | Tensile Strength (psi) | | Elongation (Percent) | | Hrs. to Failure | Crack Length (in units**) |
| | | | Day(s) | | Day(s) | | Day(s) | | | |
| | | — | 0 | 1 | 0 | 1 | 0 | 1 | 12 | 12.6 |
| 5* | None | — | — | 1380 | 3250 | 1600 | 360 | 220 | | |
| 6* | 2,2'-Methylenebis(4-methyl-6-t-butylphenol) | — | — | 1450 | 3600 | 2400 | 400 | 270 | 24 | 13.9 |
| 7* | Mixture of about 40% 2-t-butyl-4,4'-isopropylidenediphenol & about 60% 2,2'-di-t-butyl-4,4'-isopropylidenediphenol | — | — | 1500 | 3500 | 2000 | 380 | 250 | 24 | 14.0 |
| 8* | Mixture of Styrenated phenols | — | — | 1600 | 3700 | 2650 | 390 | 290 | 24 | 13.8 |
| 9* | p,p'-di-(1,1,3,3-tetramethylbutyl)diphenylamine | — | — | 1700 | 3550 | 3150 | 390 | 320 | 28 | 13.9 |
| 10 | 1-[1-Naphtho(2,1-b)furanyl]-2-naphthol | 2-Naphthol | — | 1500 | 3200 | 2400 | 360 | 280 | 16 | 13.1 |
| 11 | 1-[1-Naphtho(2,1-b)furanyl]-2-naphthol | 2-Naphthol | — | 1510 | 3600 | 2500 | 400 | 280 | 20 | 15.7 |

*Control
**1 Unit = 0.025 in.

TABLE III

Aging Characteristics of Naphthofuranylnaphthol In Natural Rubber Vulcanizates

| Ex. | Compound | Starting Naphthol | 300% Modulus Day | | | | Tensile Strength (psi) Day | | | | Ultimate Elongation (%) Day | | | |
|---|---|---|---|---|---|---|---|---|---|---|---|---|---|---|
| | | | 0 | 1 | 2 | 3 | 0 | 1 | 2 | 3 | 0 | 1 | 2 | 3 |
| 12* | None | — | 1900 | — | — | — | 2900 | 1600 | 900 | 900 | 390 | 270 | 200 | 190 |
| 13* | 2,2'-Methylenebis(4-methyl-6-t-butyl-phenol) | — | 2600 | 300 | — | — | 3900 | 3150 | 2200 | 2200 | 420 | 310 | 220 | 220 |
| 14* | Stabilizer** | — | 2000 | 2300 | 2450 | 2300 | 3200 | 2950 | 2450 | 2300 | 430 | 360 | 290 | 280 |
| 15 | 1-[6,7,8,9-Tetrahydro-1-naphtho(2,1-b)furanyl]-5,6,7,8-tetrahydro-2-naphthol | 5,6,7,8-Tetrahydro-2-naphthol | 2500 | 2800 | — | — | 3800 | 2850 | 2150 | 1700 | 420 | 310 | 240 | 190 |

*Control
**Stabilizer having the formula:

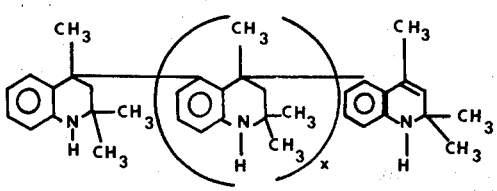

wherein x is 0 to 10

TABLE IV

Aging Characteristics of Naphthofuranylnaphthol In Natural Rubber Vulcanizates

| Ex. | Compound | Starting Naphthol | 300% Modulus Day(s) | Tensile Strength (psi) Day(s) | | | | Ultimate Elongation (%) Day(s) | | | |
|---|---|---|---|---|---|---|---|---|---|---|---|
| | | | 0 | 0 | 1 | 2 | 3 | 0 | 1 | 2 | 3 |
| 16* | None | — | 2700 | 2800 | 1300 | 600 | 550 | 310 | 180 | 150 | 120 |
| 17* | 2,2'-Methylenebis(4-methyl-6-t-butylphenol) | — | 2650 | 3400 | 2200 | 1350 | 1000 | 370 | 250 | 170 | 140 |
| 18* | t-Butylated Bisphenol A | — | 2600 | 3400 | 2450 | 1800 | 1500 | 375 | 270 | 200 | 190 |
| 19 | 1-[1-Naphtho(2,1-b)furanyl]-2-naphthol | 2-Naphthol | 2700 | 3200 | 1500 | 1200 | 1000 | 340 | 200 | 170 | 170 |

*Control

EXAMPLES 20 – 21

Examples 20 – 21 demonstrate stabilizing properties of a naphthofuranylnaphthol in uncured SN rubber. In each example, 0.68 g. of a given stabilizer was mixed with 68 g. of reprecipitated SN rubber in a Brabender Plasticorder for 2 minutes at 80°C. Each sample was prepared and tested for Mooney viscosity before and after aging according to ASTM D-1646-72 minutes using a large rotor and a 1-minute warm-up time. Mooney buttons were aged at 70°C for 10 days in an oven according to ASTM D-573-67. Test results are summarized in Table V. The Mooney viscosity data indicates that the naphthofuranylnaphthol maintains Mooney viscosity as well as or better than the control stabilizer.

EXAMPLES 22 – 25

Examples 22 – 25 demonstrate stabilizing properties of a naphthofuranylnaphthol in a styrene-acrylonitrile (SAN) copolymer composition. The SAN copolymer contained about 30% by weight acrylonitrile based upon total copolymer weight and had a weight-average molecular weight of about 118,000 and a number-average molecular weight of about 51,000. In each example, about 75 g. of SAN copolymer was mixed in a Brabender Plasticorder fitted with a cam head. Mixing was performed at 175°C and 30 rpm until fluxing occurred (typically about 1.5 minutes after mixing began). At that time, 75 g. more of SAN copolymer, and 0.75 gram of a given stabilizer were charged to the Brabender, and mixing was continued for about another 2.5 minutes. The mix was dumped, cold-pressed into sheets about 0.25 inch thick, cut into 0.25 inch cubes, pressed into 6 in. × 6 in. × 0.02 in. sheets at 175°C for about 4.5 minutes, cooled, and cut into 1 in. × 1 in. × 0.02 in. squares which were aged at 100°C in a circulating oven for varying times shown in Table VI. A Brinkman Fiber Optics Probe Colorimeter Model PC-100 was used to measure percent light transmission

TABLE V

Stabilization of SN Rubber with a Naphthofuranylnaphthol

| Ex. | Stabilizer | Starting Naphthol | Mooney Viscosity After No Aging | | | Mooney Viscosity After Aging 10 Days at 70°C | | | Average Viscosity Loss(%) |
|---|---|---|---|---|---|---|---|---|---|
| | | | Immediate | 4 Min. Shearing Time | 10 Min. Shearing Time | Immediate | 4 Min. Shearing Time | 10 Min. Shearing Time | |
| 20* | 2,6-Di-t-butyl-p-cresol | — | 75 | 65 | 62 | 65 | 58 | 55 | 12 |
| 21 | 1-[1-Naphtho(2,1-b)furanyl]-2-naphthol | 2-Naphthol | 77 | 68 | 66 | 68 | 62 | 58 | 12 |

*Control at 450 nm of heat-aged samples in comparison to unaged samples. Reduced light transmission indicates increased color development and is a measure of increased copolymer oxidation. Test results are summarized in Table VI. The data indicates the naphthofuranylnaphthol has stabilizing properties as good as or better than the control stabilizers.

cording to the procedures used for Examples 5 – 19, with 1.05 parts of accelerator and 1.1 parts of a given stabilizer being added during milling. Test results are set forth in Table VIII. The data in Table VIII indicates that the naphthofuranylnaphthols have stabilizing properties as good as or better than the control stabilizers.

TABLE VI

Stabilization of a Styrene-Acrylonitrile Copolymer with a Naphthofuranylnaphthol

| | | Starting Naphthol | % Transmission After Aging at 100°C | | | |
|---|---|---|---|---|---|---|
| | | | 0 Days | 10 Days | 50 Days | 100 Days |
| 22* | 4,4'-Butylidene-bis(6-t-butyl-m-cresol) | — | 100 | 88 | 60 | 42 |
| 23* | 1,1,3-Tris(2-methyl-4-hydroxy-5-t-butyl)butane | — | 100 | 93 | 74 | 50 |
| 24* | Mixture of tri(monononylphenyl) phosphite and tri(dinonylphenyl) phosphite | — | 100 | 94 | 66 | 43 |
| 25 | 1-[1-Naphtho(2,1-b)furanyl]-2-naphthol | 2-Naphthol | 100 | 85 | 75 | 69 |

*Control

TABLE VIII

Aging Characteristics of Naphthofuranylnaphthols in Mixed Rubber Vulcanizates

| Ex. | Stabilizer | Starting Naphthol | Test Tube Aging at 100°C Tensile Strength (Psi) | |
|---|---|---|---|---|
| | | | 0 Days | 1 Day |
| 26* | 2,2'-Methylenebis(4-methyl-6-t-butylphenol) | — | 2510 | 1800 |
| 27* | Mixture of Styrenated Phenols | — | 2720 | 1760 |
| 28 | 1-[1-Naphtho(2,1-b)furanyl]-2-naphthol | 2-Naphthol | 2680 | 1950 |
| 29 | 1-[7-t-Butyl-1-naphtho(2,1-b)furanyl]-6-t-butyl-2-naphthol | 6-t-Butyl-2-naphthol | 2690 | 1930 |

*Control

EXAMPLES 26 – 29

Examples 26 – 29 demonstrate stabilizing properties of naphthofuranylnaphthols in cured rubber vulcanizates. A masterbatch was prepared by mixing the following materials in a Banbury mixer:

TABLE VII

| Materials | Parts by Wt. |
|---|---|
| Natural Rubber | 40.0 |
| SN Rubber | 20.0 |
| Cis-polybutadiene | 20.0 |
| Styrene-butadiene Copolymer | 19.2 |
| Carbon Black | 50.0 |
| Zinc Oxide | 5.0 |
| Stearic Acid | 1.5 |
| Filler | 2.0 |
| Paraffinic Oil | 5.0 |
| Sulfur | 3.3 |
| Antioxidant | 0.5 |
| Bactericide | 0.1 |
| | 166.6 |

Compounding, curing and testing were performed ac-

EXAMPLES 30 – 33

Examples 30 – 33 demonstrate stabilizing properties of naphthofuranylphenols in white cured rubber vulcanizates. A masterbatch was prepared by mixing the following materials in a Banbury mixer:

TABLE IX

| Materials | Parts by Wt. |
|---|---|
| Natural Rubber | 100.0 |
| TiO$_2$ | 50.0 |
| Zinc Oxide | 5.0 |
| Stearic Acid | 2.0 |
| Sulfur | 2.75 |
| | 159.75 |

Compounding, curing and testing were performed according to the procedures used for Examples 5 – 19, with 1.0 part of mercaptobenzothiazole disulfide and 0.1 part of tetramethylthiuram disulfide being added during milling. Test results are set forth in Table X. The data in Table X indicates that the naphthofuranylnaphthols have stabilizing properties about the same as the control stabilizers.

TABLE X

Aging Characteristics of Naphthofuranylnaphthols in White Rubber Vulcanizates

| Ex. | Stabilizer | Starting Naphthol | Test Tube Aging at 100°C | | | % Loss of Tensile Strength after 3 Days |
|---|---|---|---|---|---|---|
| | | | Tensile Strength (psi) | | | |
| | | | 0 Days | 1 Day | 3 Days | |
| 30* | P,P'-dioctyldiphenylamine | — | 1800 | 1350 | 750 | 58% |
| 31* | 1-Dimethylaminomethyl-2-naphthol | — | 1100 | 700 | 200 | 81% |

TABLE X-continued

Aging Characteristics of Naphthofuranylnaphthols in White Rubber Vulcanizates

| Ex. | Stabilizer | Starting Naphthol | Test Tube Aging at 100°C | | | |
|---|---|---|---|---|---|---|
| | | | Tensile Strength (psi) | | | % Loss of Tensile Strength after 3 Days |
| | | | 0 Days | 1 Day | 3 Days | |
| 32 | 1-[1-Naphtho(2,1-b)furanyl]-2-naphthol | 2-Naphthol | 1900 | 750 | 500 | 73% |
| 33 | 1-[4,7-Di-t-butyl-1-naphtho(2,1-b)furanyl]-3,6-di-t-butyl-2-naphthol | 3,6-Di-t-Butyl-2-naphthol | 1250 | 1000 | 450 | 66% |

*Control

I claim:

1. A stabilized composition comprising 100 parts by weight of an organic material subject to the deleterious effects of oxygen, heat and light and from about 0.1 part to about 10 parts by weight of at least one naphthofuranylnaphthol having the formula

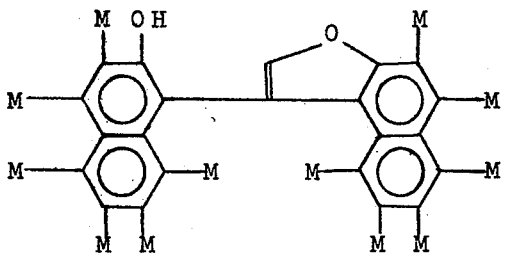

wherein each M is hydrogen, halogen, or an alkyl group containing from one to eight carbon atoms.

2. A composition of claim 1 wherein the organic material is a polymer.

3. A composition of claim 2 wherein the polymer is a dienic polymer.

4. A composition of claim 3 wherein at least six M's are hydrogen and each of the remaining M's is bromo, chloro or an alkyl group containing from one to eight carbon atoms.

5. A composition of claim 4 wherein each of the remaining M's is an alkyl group containing from one to four carbon atoms.

6. A composition of claim 5 wherein said dienic polymer is an isoprene homopolymer or copolymer.

7. A composition of claim 6 wherein said dienic polymer is polyisoprene.

8. A composition of claim 2 wherein at least six M's are hydrogen and each of the remaining M's is bromo, chloro or an alkyl group containing from one to eight carbon atoms.

9. A composition of claim 8 wherein each of the remaining M's is an alkyl group containing from one to four carbon atoms.

10. A vulcanized composition of claim 3.

11. A composition of claim 3 wherein said naphtholfuranylnaphthol is 1-[1-naphtho(2,1-b)furanyl]-2-naphthol.

12. A composition of claim 3 wherein said naphtholfuranylnaphthol is 1-[7-t-butyl-1-naphtho(2,1-b)furanyl]-6-t-butyl-2-naphthol.

13. A composition of claim 3 wherein said naphthofuranylnaphthol is 1-[4,7-di-t-butyl-1-naphtho(2,1-b)furanyl]-3,6-di-t-butyl-2-naphthol.

14. A composition of claim 3 wherein said naphthofuranylnaphthol is 1-[6,7,8,9-tetrahydro-1-naphtho(2,1-b)furanyl]-5,6,7,8-tetrahydro-2-naphthol.

15. A composition of claim 2 wherein the polymer contains polymerized therein (1) from about 50% to about 90% by weight based upon total copolymer weight of styrene, or at least one alkyl styrene, alkoxy styrene or halostyrene, or a mixture thereof, wherein the alkyl or alkoxy group contains from one to eight carbon atoms, (2) from about 10% to about 50% by weight based upon total copolymer weight of at least one vinyl nitrile having the formula

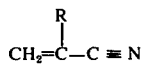

wherein R is hydrogen or an alkyl radical containing from one to three carbon atoms, and (3) from 0% to about 20% by weight of at least one other monoolefin.

16. A composition of claim 15 wherein at least 6 M's are hydrogen and each of the remaining M's is bromo, chloro or an alkyl group containing from one to eight carbon atoms.

17. A composition of claim 16 wherein each of the remaining M's is an alkyl group containing from one to four carbon atoms.

18. A composition of claim 15 wherein said naphthofuranylnaphthol is 1-[1-naphtho(2,1-b)furanyl]-2-naphthol.

19. A naphthofuranylnaphthol having the formula

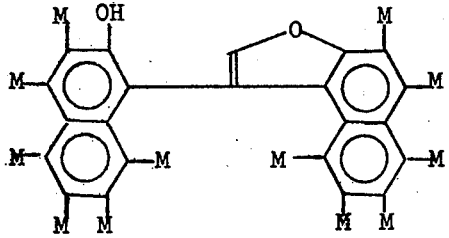

wherein at least eight M's are hydrogen but at least two of the remaining M's are alkyl groups containing from one to four carbon atoms.

20. A naphtholfuranylnaphthol of claim 19, 1-[7-t-butyl-1-naphtho(2,1-b)furanyl]-6-t-butyl-2-naphthol.

21. A naphthofuranylnaphthol of claim 19, 1-[4,7-di-t-butyl-1-naphtho(2,1-b)furanyl]-3,6-di-t-butyl-2-naphthol.

22. 1-[6,7,8,9-tetrahydro-1-naphtho(2,1-b)furanyl]-5,6,7,8-tetrahydro-2-naphthol.

* * * * *